United States Patent
Ellis et al.

(10) Patent No.: US 10,801,982 B2
(45) Date of Patent: Oct. 13, 2020

(54) GRAPHITIC CARBON NITRIDE SENSORS

(71) Applicant: University of Pittsburgh—Of the Commonwealth System of Higher Education, Pittsburgh, PA (US)

(72) Inventors: James Edward Ellis, Pittsburgh, PA (US); Alexander Star, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 141 days.

(21) Appl. No.: 16/023,630

(22) Filed: Jun. 29, 2018

(65) Prior Publication Data
US 2019/0003998 A1    Jan. 3, 2019

Related U.S. Application Data

(60) Provisional application No. 62/526,747, filed on Jun. 29, 2017.

(51) Int. Cl.
*G01N 27/12*    (2006.01)
*H01L 31/032*    (2006.01)
(Continued)

(52) U.S. Cl.
CPC ......... *G01N 27/125* (2013.01); *G01N 27/127* (2013.01); *G01N 27/4141* (2013.01);
(Continued)

(58) Field of Classification Search
CPC ............... G01N 27/125; G01N 27/127; G01N 33/0036; G01N 27/4141; G01N 33/004;
(Continued)

(56) References Cited

U.S. PATENT DOCUMENTS 4,322,682 A * 3/1982 Schadwill .......... G01R 1/07328
                                                324/750.25
5,329,692 A * 7/1994 Kashiwagi ......... H05K 13/0452
                                                29/740
(Continued)

FOREIGN PATENT DOCUMENTS

EP            2848927 A1    3/2015
WO    WO2012118948 A1    9/2012

OTHER PUBLICATIONS

Alves, Diego C.B. et al.; Cooper Nanoparticles Stabilized by Reduced Graphene Oxide for CO2 reduction Reaction; Matter Renew Sustain Energy (2015) 4:2, 2-7.
(Continued)

*Primary Examiner* — Giovanni Astacio-Oquendo
(74) *Attorney, Agent, or Firm* — Bartony & Associates LLC

(57) ABSTRACT

A sensor includes a substrate, a first electrode, a second electrode spaced from the first electrode, and a sensing medium on the substrate between the first electrode and the second electrode. The sensor medium includes a functionalized graphitic material and an uncondensed graphitic carbon nitride disposed upon the functionalized graphitic material. The sensor further includes a system for applying electromagnetic energy to the sensing medium to increase the conductance of the sensing medium, and circuitry including at least one measurement system in operative connection with the sensor to measure a variable relatable to the conductance of the sensing medium which is dependent upon the presence of an analyte to be detected.

24 Claims, 12 Drawing Sheets

(51) Int. Cl.
   *G01N 33/00* (2006.01)
   *G01N 27/414* (2006.01)
   *H01L 31/113* (2006.01)
(52) U.S. Cl.
   CPC ....... *G01N 33/004* (2013.01); *G01N 33/0036* (2013.01); *H01L 31/0324* (2013.01); *H01L 31/113* (2013.01); *G01N 27/4146* (2013.01)
(58) Field of Classification Search
   CPC ............ G01N 27/4146; H01L 31/0324; H01L 31/113
   USPC ................................ 324/693, 691, 649, 600
   See application file for complete search history.

(56) References Cited

U.S. PATENT DOCUMENTS

| | | | |
|---|---|---|---|
| 5,506,510 A * | 4/1996 | Blumenau | G01R 1/07378 324/149 |
| 5,518,603 A | 5/1996 | Furuhashi | |
| 5,597,762 A * | 1/1997 | Popovici | H01J 9/022 438/105 |
| 5,616,825 A | 4/1997 | Achey | |
| 8,574,536 B2 * | 11/2013 | Boudou | C09K 11/65 423/446 |
| 8,632,665 B2 | 1/2014 | Eckhardt | |
| 8,702,936 B2 | 4/2014 | Lemaire | |
| 8,920,764 B2 | 12/2014 | Star | |
| 9,482,638 B2 | 11/2016 | Star | |
| 2012/0018303 A1 | 1/2012 | Bordo | |
| 2013/0040283 A1 * | 2/2013 | Star | G01N 27/127 435/5 |

OTHER PUBLICATIONS

Chen, Ke et al.; Catalyst-Free Growth of Three-Dimensional Graphene Flakes and Graphene/g-C3N4 Composite for Hydrocarbon Oxidation, ACS Nano 2016, 10, 3665-3673.

Duan, Jingjing et al.; Porous C3N4 Nanolayers@N-Graphene Films as Catalyst Electrodes for Highly Efficient Hydrogen Evolution; ACS Nano, vol. 9, No. 1 (2015), 931-940.

Kofuji, Yusuke et al.; Carbon Nitride—Aromatic Diimide—Graphene Nanohybrids: Metal-Free Photocatalysts for Solar-to-Hydrogen Peroxide Energy Conversion with 0.2% Efficiency; J. Am. Chem. Soc. 2016, 138, 10019-10025.

Li, Yibing et al.; Cross-Linked g-C3N4 / rGO Nanocomposites with Tunable Band Structure and Enhanced Visible Light Photocatalytic Activity; small 2013, 9, No. 19, 3336-3344.

Ong, Wee-Jun et al.; Graphene oxide as a structure-directing agent for the two-dimensional interface engineering of sandwich-like graphene-g-C3N4 hybrid nanostructures with enhanced visible-light photoreduction of CO2 to methane; Chem Commun. (2015), 51, 858-861.

Hang, Nguyen Thuy et al.; Efficient exfoliation of g-C3N4 and NO2 sensing behavior of graphene / g-C3N4 nanocomposite; Sens. Actuator B 2017, 248, 940-948.

Tian, Jingqi et al.; Three-Dimensional Porous Supramolecular Architecture from Ultrathin g-C3N4 Nanosheets and Reduced Graphene Oxide: Solution Self-Assembly Construction and Application as a Highly Efficient Metal-Free Electrocatalyst for Oxygen Reduction Reaction; ACS Appl, Mater. Interlaces 2014, 6, 1011-1017.

* cited by examiner

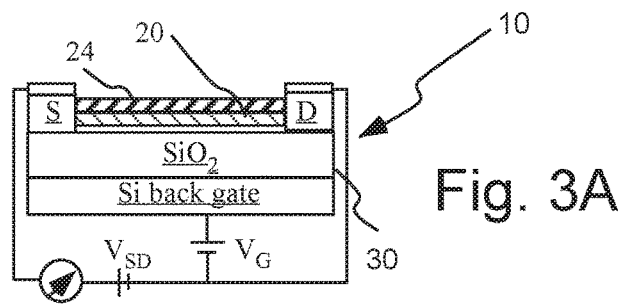
Fig. 3A
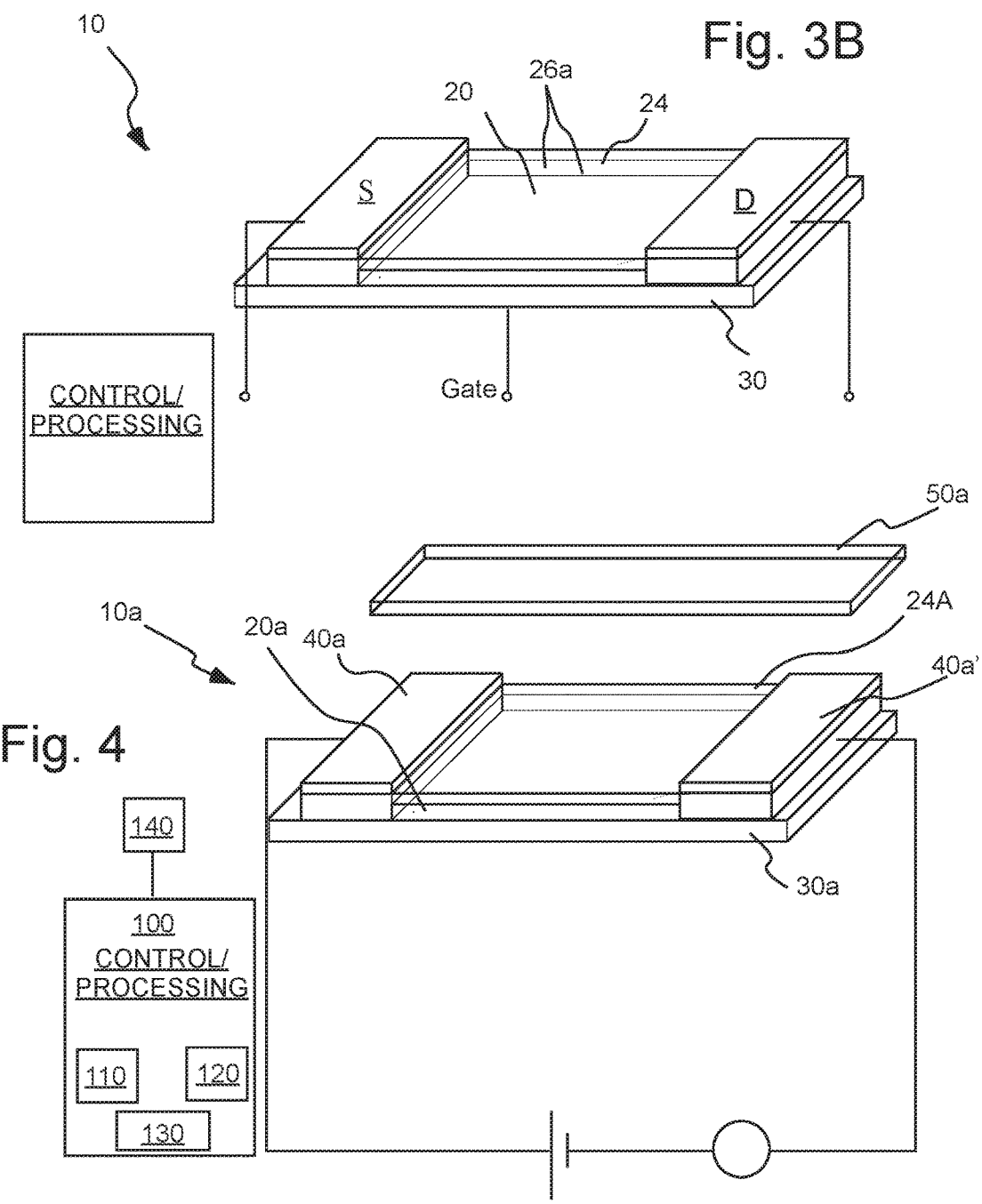
Fig. 3B
Fig. 4

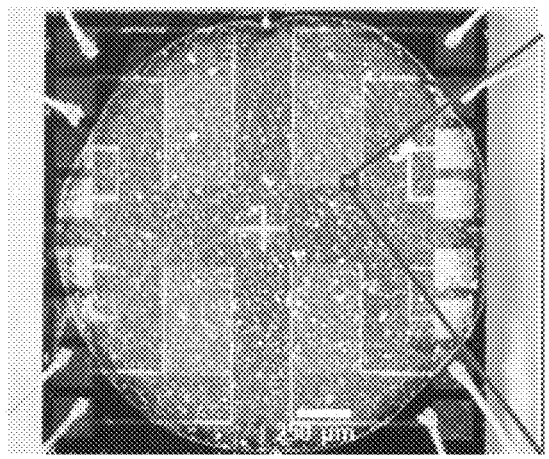 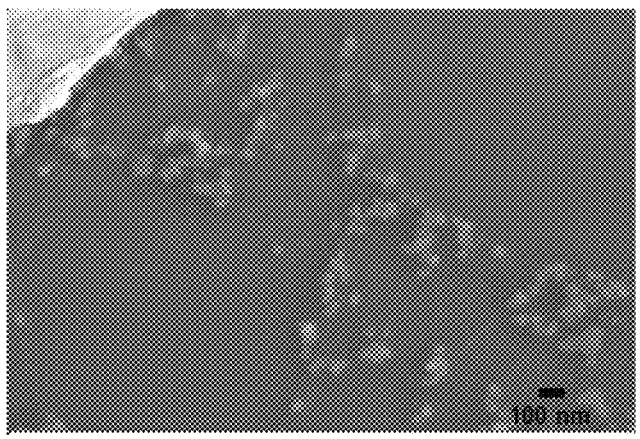
Fig. 5A  Fig. 5B
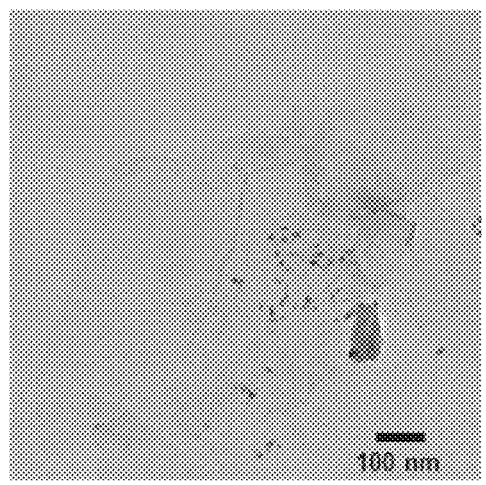
Fig. 5C

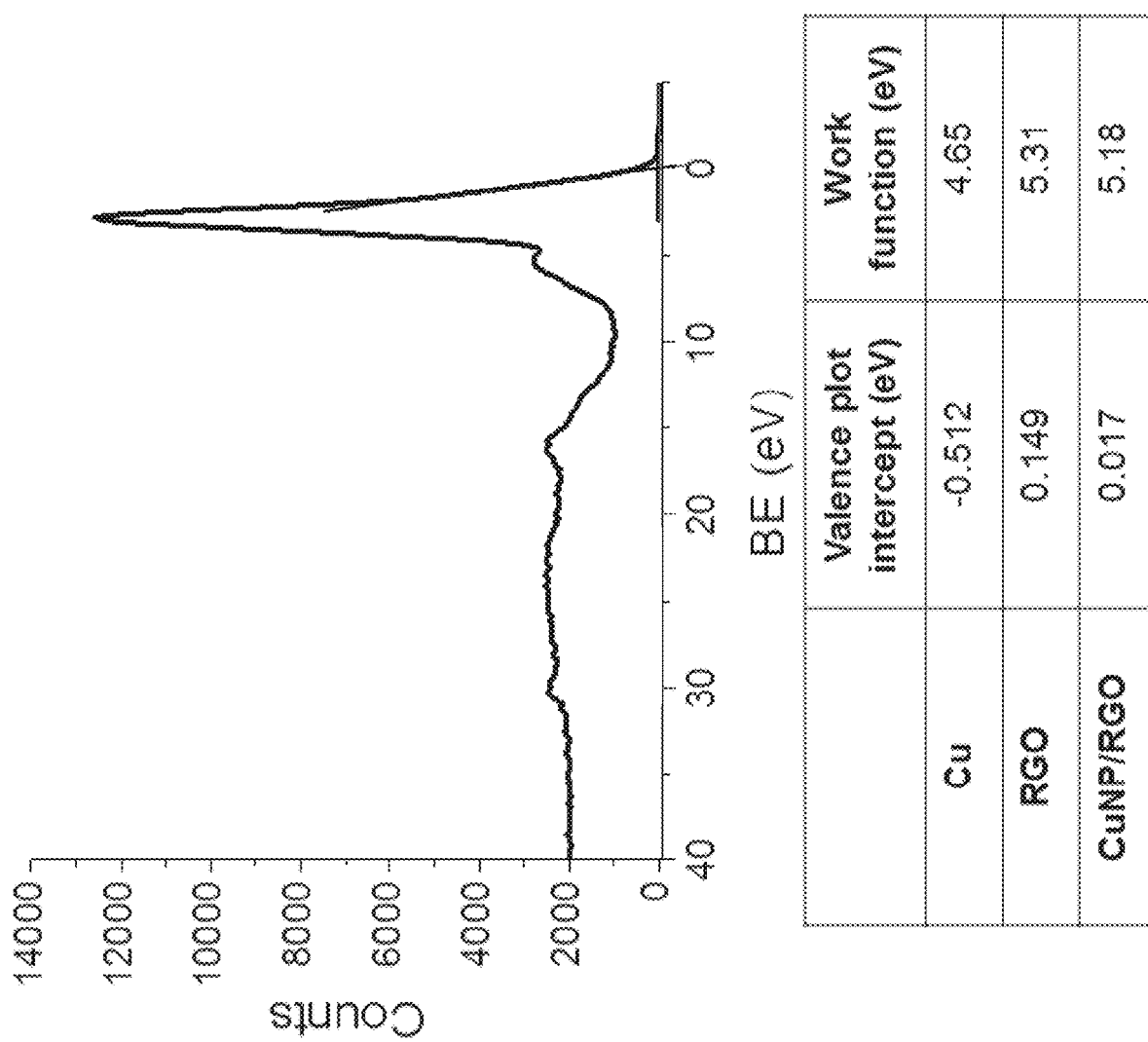

GRAPHITIC CARBON NITRIDE SENSORS

CROSS-REFERENCE TO RELATED APPLICATIONS

This application claims benefit of U.S. Provisional Patent Application Ser. No. 62/526,747, filed Jun. 29, 2017, the disclosure of which is incorporated herein by reference.

GOVERNMENTAL INTEREST

This invention was made with government support under grant no. TR000005 awarded by the National Institutes of Health (NIH). The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

The ability to detect and quantify the concentration of a specific target gas is an important resource for a variety of fields including medical, industry, and security. For example, molecular oxygen is a target of interest because of its ubiquity in the environment, in diverse industrial and mechanical processes, and in biological systems. For example, oxygen sensors have been deployed in automobiles and other combustion systems to determine the combustion efficiency, since inefficient combustion is directly related with harmful gas emissions. Alternatively, dissolved oxygen concentration in cell cultures is an important physiological factor that would be beneficial to sense. For example, hypoxia in tissue cells has been found to correlate with an acceleration of disease progression, including tumor growth. Such examples illustrate the wide-ranging conditions (e.g. gas vs. solution, high vs. low pressure, etc.) for oxygen sensing applications that drive the development of novel sensing materials and call for an understanding and optimization of their associated working mechanisms.

The research area of gas sensor development has benefitted from and grown alongside the rise of nanomaterials and of nano-characterization techniques. In addition, sensor material research has borrowed and adapted many findings from the heterogeneous catalysis field. Common heterogeneous catalyst materials (for example, metal nanoparticles and metal oxides) have shown excellent sensor properties when coupled with good transducer materials such as carbon nanotubes or graphene. Catalytic materials provide a receptor function by adsorbing and reacting with certain analytes, while changes in the local chemical environment and minute charge transfers are able to effect observable changes in a carbon nanomaterial's electrical properties as a result of its large charge carrier mobility and high surface area to volume ratio. Optimizing receptor/transducer interfaces and choosing receptors that have complementary work functions with the transducer are important strategies for improving sensor sensitivity.

Semiconductor photocatalysts are a class of heterogeneous catalysts that utilize photo-generated electron-hole pairs for photoredox catalysis. One such photocatalyst, "graphitic" carbon nitride, is a metal-free semiconductor that has a planar, sheet-like morphology similar to graphene. Carbon nitride's bandgap (2.7 eV) is beneficial because of its ability to be photoexcited by visible light. Carbon nitride also has the proper band structure to catalyze multiple redox reactions. It has, for example, demonstrated activity toward water splitting, $H_2O_2$ activation, oxygen reduction reaction (ORR), and $CO_2$ reduction. Graphitic carbon nitride is produced, for example, by thermally polymerizing cyanamide, dicyandiamide, or melamine at temperatures ranging from 500-600° C. Depending on the precursor and synthetic parameters, the resulting structure may be composed of heptazine or triazine units with different degrees of condensation (condensed-$C_3N_4$; uncondensed-$C_6N_9H_3$).

The uncondensed form of graphitic carbon nitride, known as melon, was initially speculated to be a linear polymer of heptazine units connected by secondary amine linkages. Structural characterization of melon has found that hydrogen bonding and the presence of n-stacking between polymer units results in its graphitic-like morphology. The weak interplanar interactions existent between sheets allow exfoliation of bulk carbon nitride into carbon nitride nanosheets or quantum dots. Both of these derivative carbon nitride nanomaterials have properties differing from bulk carbon nitride that include an increased bandgap, an increase of the specific surface area, an improved electron transport ability along the in-plane direction, and increased lifetimes of photoexcited charge carriers as a result of the quantum confinement effect. Despite these improvements, carbon nitride still suffers from a fast recombination rate, which limits its use as a photocatalyst.

Hybridization of carbon nitride with carbon nanomaterials has been shown to promote fast separation of photoinduced charge carriers, resulting in a slower recombination rate and increased photocatalytic activity. As an electrocatalyst, carbon nitride hybridized with graphene or carbon nanotubes has shown catalytic activity for the hydrogen evolution reaction (HER) and the oxygen reduction reaction (ORR). The presence of carbon nanomaterials does not inhibit photoexcitation of carbon nitride. Graphene has been used as a support as well as a cross-linker to prepare effective photodegradation catalysts. Carbon nitride on reduced graphene oxide (rGO) can photocatalytically reduce oxygen to hydrogen peroxide, a potential solar fuel, in the presence of water.

SUMMARY

In one aspect, a sensor includes a substrate, a first electrode, a second electrode spaced from the first electrode, and a sensing medium on the substrate between the first electrode and the second electrode. The sensor medium includes a functionalized graphitic material and an uncondensed graphitic carbon nitride disposed upon the functionalized graphitic material. The sensor further includes a system for applying electromagnetic energy to the sensing medium to increase the conductance of the sensing medium, and circuitry including at least one measurement system in operative connection with the sensor to measure a variable relatable to the conductance of the sensing medium which is dependent upon the presence of an analyte to be detected.

In a number of embodiments, the functionalized graphitic material includes oxygen functional groups. The functionalized graphitic material may, for example, be reduced graphene oxide or holey reduced graphene oxide. In a number of embodiments, the functionalized graphitic material is holey reduced graphene oxide. In a number of embodiments, the functionalized graphitic material is reduced graphene oxide. In a number of embodiments wherein the functionalized graphitic material is holey reduced graphene oxide, the hole size of the holey reduced graphene oxide may, for example, be within a predetermined range to provide a band gap within a predetermined range to determine an identity of the analyte. The hole size in the holey reduced graphene oxide may, for example, be 1 nm or greater.

In a number of embodiments, the analyte is oxygen. As described above, the functionalized graphitic material for such an oxygen sensor may, for example, be reduced graphene oxide or holey reduced graphene oxide.

The system for applying electromagnetic energy may, for example, be configured to apply UV light energy, visible light energy or electrical energy. In a number of embodiments, the system for applying electromagnetic energy is configured to apply UV light energy.

The sensor may further include a humidity sensor. In a number of embodiments, the sensor further includes a source of water (to, for example, provide a relative humidity in the vicinity of or in the microenvironment of the sensing medium within a predetermined range).

In a number of embodiments, one or more materials or compositions may be deposited upon the functionalized graphitic materials to, for example, modify the work function of the resulting composite material. Modification of the composite materials hereof, may, for example, enable sensing of different analytes. In a number of embodiments, metal nanoparticles or inorganic semiconductor nanoparticles are deposited upon the functionalized graphitic material. In a number of embodiments, the metal nanoparticles comprise copper and the analyte is carbon dioxide.

In another aspect, a method of sensing an analyte includes providing a sensor system including a substrate, a first electrode, a second electrode spaced from the first electrode, and a sensing medium on the substrate between the first electrode and the second electrode, wherein the sensor medium includes a functionalized graphitic material and an uncondensed graphitic carbon nitride disposed upon the functionalized graphitic material, applying electromagnetic energy to the sensing medium to increase the conductance of the sensing medium, and measuring a variable relatable to the conductance of the sensing medium which is dependent upon the presence of an analyte to be detected. In a number of embodiments, the analyte is oxygen.

The functionalized graphitic material may, for example, include oxygen functional groups. As described above, the functionalized graphitic material may, for example, be reduced graphene oxide or holey reduced graphene oxide. In a number of embodiments, wherein the functionalized graphitic material is holey reduced graphene oxide, the hole size of the holey reduced graphene oxide may, for example, be controlled or selected to be within a predetermined range to provide a band gap within a predetermined range to determine an identity of the analyte. The hole size in the holey reduced graphene oxide may, for example, be 1 nm or greater.

As also described above, applying electromagnetic energy may, for example, include applying UV light energy, visible light energy or electrical energy. In a number of embodiments, UV light energy is applied.

The method may further include measuring humidity in the environment surrounding the sensing medium. In a number of embodiments, the method further includes providing water to increase the humidity in the environment surrounding the sensing medium.

As described above, the method may further include depositing one or more materials upon the functionalized graphitic materials to, for example, modify the work function of the resulting composite material. In a number of embodiments, metal nanoparticles or inorganic semiconductor nanoparticles are deposited upon the functionalized graphitic material. In a number of embodiments, the metal nanoparticles comprise copper and the analyte is carbon dioxide.

In a further aspect, an oxygen sensor includes a substrate, a first electrode, a second electrode spaced from the first electrode, and a sensing medium on the substrate between the first electrode and the second electrode. The sensor medium includes a functionalized graphitic material and an uncondensed graphitic carbon nitride disposed upon the functionalized graphitic material. The oxygen sensor further includes a system for applying electromagnetic energy to the sensing medium to increase the conductance of the sensing medium and circuitry including at least one measurement system in operative connection with the sensor to measure a variable relatable to the conductance of the sensing medium which is dependent upon the presence of oxygen. As described above, electromagnetic energy in the form of UV light energy, visible light energy or electrical energy may be applied. In a number of embodiments of an oxygen sensor, UV light energy is applied.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 3A illustrates schematically an embodiment of a sensor hereof which is operable as a field effect transistor or FET.

FIG. 3B illustrates a perspective schematic view of a portion of the sensor of FIG. 3A.

FIG. 4 illustrates a perspective schematic view of an embodiment of a sensor hereof which is operable as a chemiresistor.

FIG. 5A illustrates an optical image of an embodiment of a carbon nitride/reduced graphene oxide (rGO) sensor chip hereof for oxygen sensing with a graphitic carbon nitride/rGO sensing medium: (A).

FIG. 5B illustrates a scanning electron microscope (SEM) image of rGO decorated with carbon nitride nanoparticles or NPs between two Au electrodes.

FIG. 5C illustrates a TEM image of carbon nitride-decorated rGO.

FIG. 8 illustrates a valence XPS spectrum of Cu NP/RGO and a table of Cu, RGO, and Cu NP/RGO work functions.

DETAILED DESCRIPTION

Figure 1A:
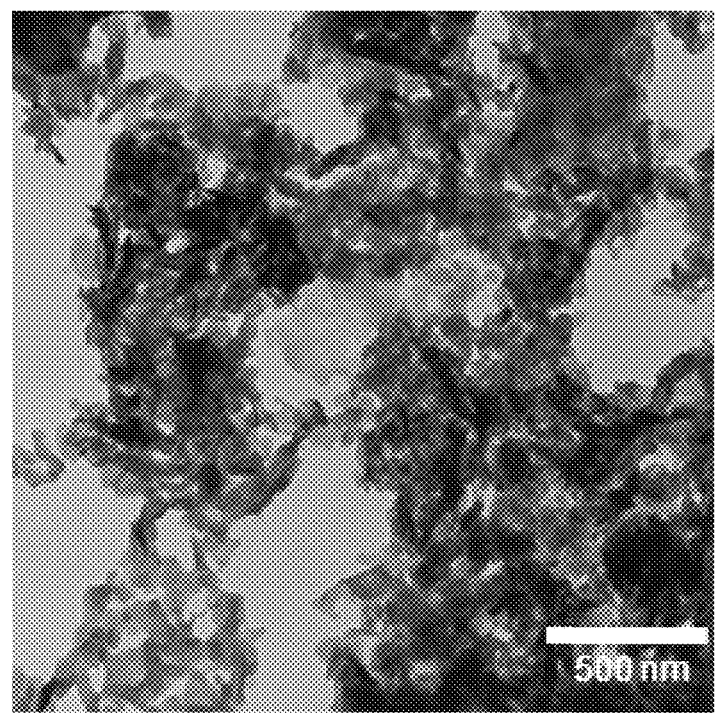
FIG. 1A illustrates characterization of synthesized graphitic carbon nitride via a transmission electron microscopy or TEM image of exfoliated graphitic-carbon nitride to form carbon nitride NP's.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensing medium" includes a plurality of such sensing media and equivalents thereof known to those skilled in the art, and so forth, and reference to "the sensing medium" is a reference to one or more such sensing media and equivalents thereof known to those skilled in the art, and so forth. Recitation of ranges of values herein are merely intended to serve as a shorthand method of referring individually to each separate value falling within the range. Unless otherwise indicated herein, each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "control system" or "controller," as used herein includes, but is not limited to, any circuit or device that coordinates and controls the operation of, for example, one or more input or output devices. For example, a controller can include a device having one or more processors, microprocessors, or central processing units (CPUs) capable of being programmed to perform input or output functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

As used herein, the term "holey reduced graphene oxide" refers to a semiconductive composition of reduced graphene oxide having holes in the base plane thereof. In a number of embodiments, the holes may, for example, have an average diameter of 1 nm or greater. The formation and characteristics of holey graphene oxide are discussed in U.S. Pat. Nos. 8,920,764 and 9,482,638, the disclosures of which are incorporated herein by reference.

In a number of embodiments hereof, a carbon nitride/reduced graphene oxide (rGO) sensor (for example, in the form of a chemiresistor or a field effect transistor) is functional to monitor a generated charge separation and subsequent oxygen reduction at the solid-gas interface. The sensor may, for example, be used as an oxygen sensor wherein the electrical response of the sensor is logarithmically proportional to oxygen concentration. In a number of embodiments, holey reduced graphene oxide or HGO may be used in connection with carbon nitride.

Sensor response (for example, sensitivity and/or selectivity) and analyte determination may, for example, be controlled by independently controlling the properties of the graphitic carbon nitride and the reduced graphene oxide of the sensing medium complex. For example, the degree of condensation of the graphitic carbon nitrides may be changed and/or the degree of functionality of the reduced graphene oxide may be changed. In the case of HGO, the band gap and/or electronic structure of the composite material may be adjusted through control of the hole size and frequency of the HGO, thereby providing a mechanism to detect the presence of a number of different analytes. The proposed mechanism for this composite material includes charge transfer from the carbon nitride layer conduction band to the graphitic layer conduction. Holes in the graphitic layer may elevate its conduction band minimum, which may change the selectivity of the material from, for example, the $O_2/H_2O$ half reaction (0.82 V vs. NHE, pH 7) to the $CO_2/CH_4$ half reaction (−0.24 V vs. NHE, pH 7). Since the conduction band minimum is proportional to the neck width of HGO, control of hole size diameter provides manipulation of this electronic property.

In a number of representative embodiments, an uncondensed graphitic carbon nitride (for example, melon) coupled to a graphitic material including functionality which interacts with the graphitic carbon nitride (for example, oxygen functionality, nitrogen functionality etc.) such as rGO or HGO is used to sense oxygen gas within the concentration range of, for example, approximately 300-10,000 ppm. For example, such functionalities on rGO increase charge transfer between the carbon nitride layer and the graphitic layer. Through x-ray diffraction or XRD, fluorescence spectroscopy, and x-ray photoelectron spectroscopy or XPS characterization it was determined that the as-synthesized carbon nitride material was heptazine-based uncondensed graphitic carbon nitride (gh-$C_6N_9H_3$). XPS characterization, especially $N_{1s}$ XPS, provided structural insight into melon's H-bridges. The $N_{1s}$ peak centered at 403.8 eV was found to be correlated with H-bridges that transfer their proton between tautomerizing N groups. The as-synthesized carbon nitride material was exfoliated into nanosheets via bath sonication, which proved to have an advantageous effect toward sensing application. Carbon nitride/rGO chemiresistor devices were prepared and tested for oxygen sensitivity in humid and dry conditions with and without UV irradiation. UV irradiation doubled the measured conductance of the carbon nitride/rGO chemiresistor as a result charge transfer of photoexcited electrons from carbon nitride nanosheets to the rGO transducer. The carbon nitride/rGO chemiresistor significantly dropped in conductance whenever exposed to oxygen gas in humid conditions and under UV irradiation. A photoredox mechanism wherein water is oxidized on the carbon nitride surface and oxygen is reduced on the rGO surface explains the chemiresistor behavior observed. The chemiresistor's response to oxygen was found to be logarithmically proportional to oxygen concentration in the range 300-10,000 ppm. A close electrical interface between two materials like the one observed in this work may be a desirable feature for sensing, photocatalysts, and photovoltaic applications.

Carbon nitride/rGO's oxygen sensitivity was tested at, for example, 100%, 75%, 45%, and 11% relative humidity or RH. Identical response to $O_2$ were observed at 100%, 75%, and 45%. However, a significant loss in sensor response was observed for 11% RH. Humidity is an important component for the sensing mechanism, and while it has been shown that the sensor can operate down to at least 45% RH at room temperature, a minimum humidity for operation has not yet been established. In very low humidity environments, a source of water may, for example, be provided to ensure suitable relative humidity in the microenvironment of the sensor.

Figure 1B:
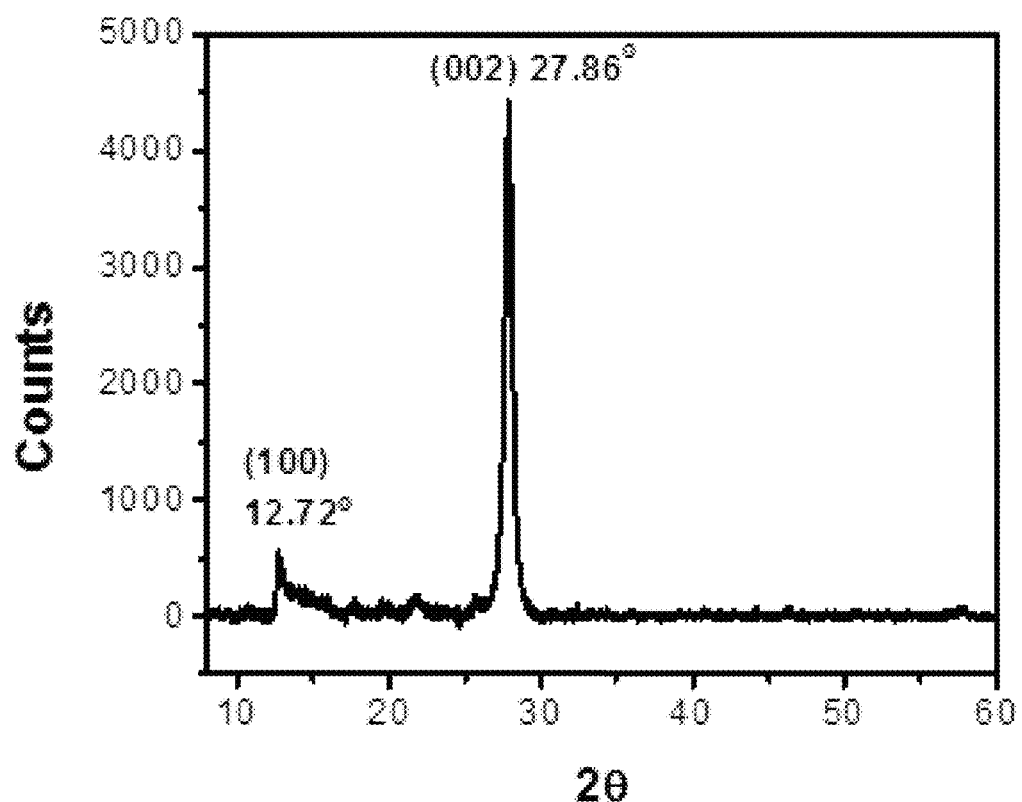
FIG. 1B illustrates XRD of as-synthesized carbon nitride material.
Figure 1C:
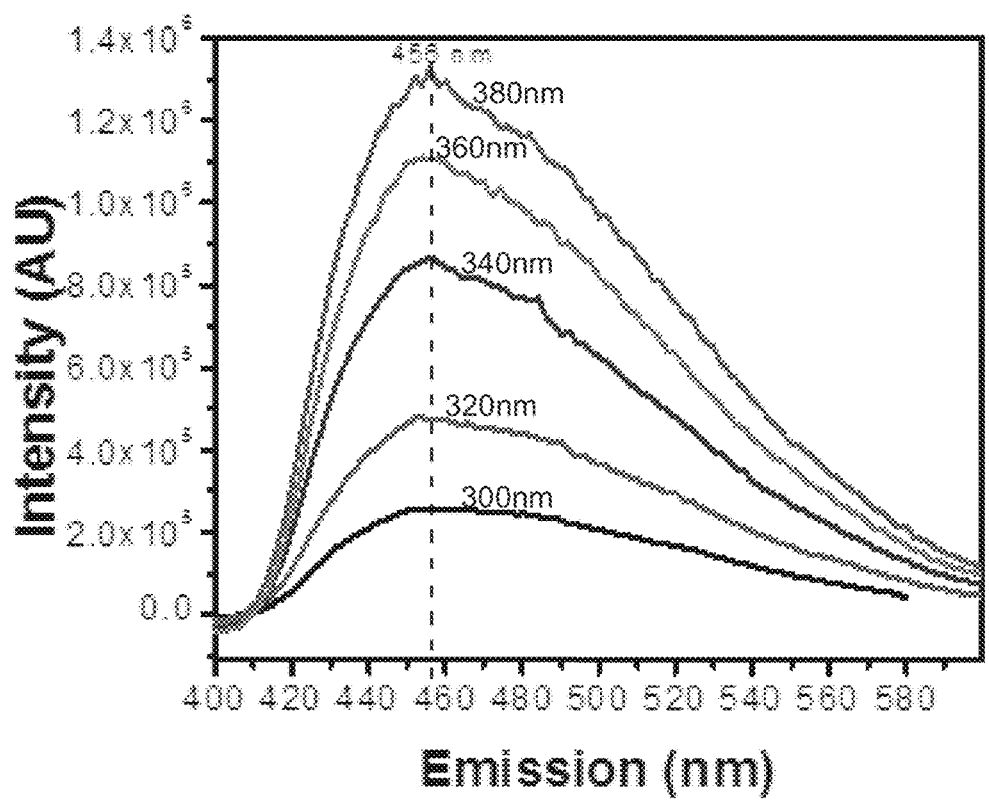
FIG. 1C illustrates fluorescence spectra of as-synthesized carbon nitride powder at different excitation wavelengths (300 nm, 320 nm, 340 nm, 360 nm, and 380 nm).
Figure 1D:
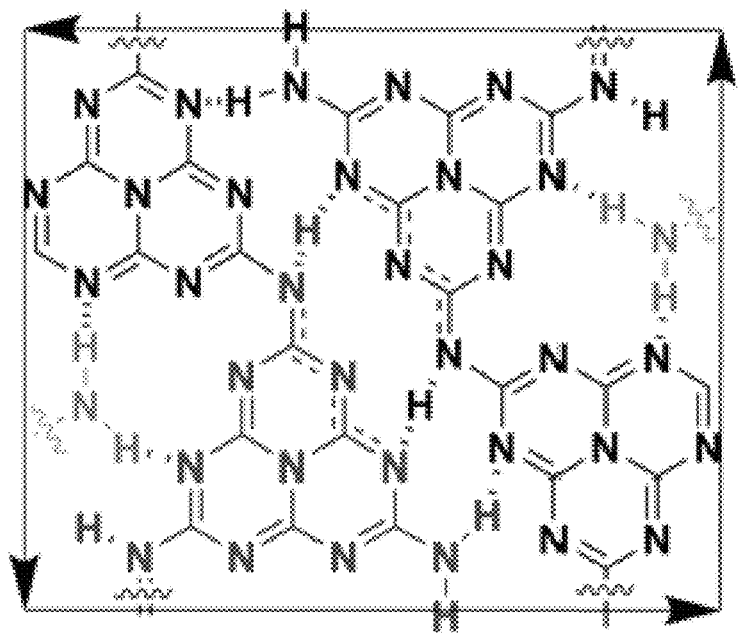
FIG. 1D illustrates unit cell of uncondensed graphitic carbon nitride with heptazine monomer (gh-$C_6N_9H_3$).

As described above, characterization of the as-synthesized carbon nitride material was performed to determine whether the material was heptazine- or triazine-based, as well as whether it was condensed or uncondensed (see FIGS. 1A-1F). Powder x-ray diffraction or PXRD of the as-synthesized material displayed a pattern indicative of layered, graphitic-like sheets (FIG. 1B). Since melamine is an intermediate of "graphitic" carbon nitride synthesis, the absence of melamine peaks indicates that reaction went to full completion. The calculated d-spacing of the material is 3.202 Å, which matches with the d-spacing for uncondensed, heptazine-based, graphitic carbon nitride (gh-$C_6N_9H_3$). Triazine-based graphitic-carbon nitride and condensed carbon nitride (g-$C_3N_4$) have larger d-spacings of 3.3-3.4 Å. The fluorescence emission of the as-synthesized material was measured in the range (300-380 nm) of long-wave UV excitation wavelengths (FIG. 1C). The emission peak is centered at 456 nm (2.72 eV) for each excitation wavelength, which corresponds well with the bandgap for pristine gh-$C_6N_9H_3$. The bandgap size of gh-$C_6N_9H_3$ is unique for non-metal materials since it is wide enough to photocatalyze numerous redox pairs, yet narrow enough to absorb visible light. Since proximate $^1H$ atoms are necessary for $^{13}C$ and $^{15}N$ CP-MAS solid-state NMR, the appearance of solid-state NMR peaks for the as-synthesized carbon nitride material supports the uncondensed structure of the material. The shifts of the peaks match well with previous literature examples.

Figure 1E:
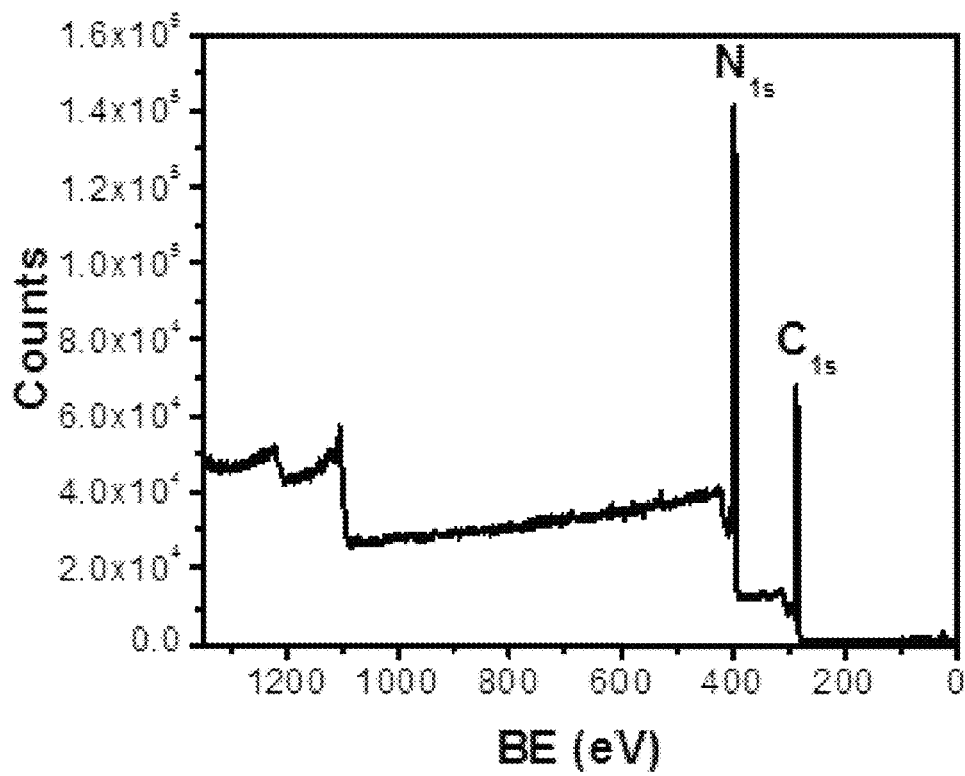
FIG. 1E illustrates a survey scan of as-synthesized carbon nitride material which exhibits an $N_{1s}$ peak (60 atomic %) and a $C_{1s}$ peak (40 atomic %); $H_{1s}$ cannot be detected with XPS.
Figure 1F:
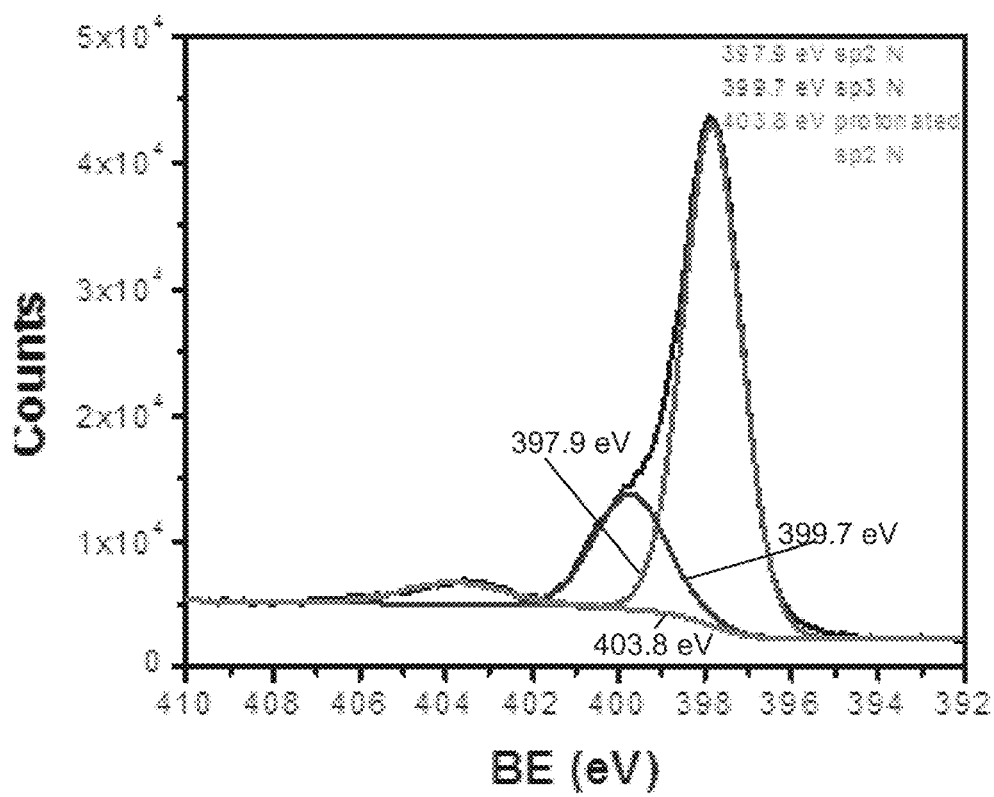
FIG. 1F illustrates a high-resolution scan of the $N_{1s}$ peak showing three deconvolved peaks: protonated sp2 N (403.8 eV), sp3 N (399.7 eV), and sp2 N (397.9 eV), wherein the $sp^3$ to $sp^2$ N ratio is ~2:7, which matches the unit cell N ratio.

XPS of the as-synthesized carbon nitride material confirmed the chemical structure of the material by providing the C to N ratio and the ratio of $sp^2$ N to $sp^3$ N (FIGS. 1E, F). Two peaks, $C_{1s}$ and $N_{1s}$, appear on the low-resolution survey XPS scan. No elemental impurities are detected. The ratio of carbon to nitrogen is 2C:3N, which is the empirical formula for uncondensed graphitic carbon nitride ($C_2N_3H$). Condensed graphitic carbon nitride (g-$C_3N_4$), on the other hand, has a C:N ratio of 3:4. The high-resolution $N_{1s}$ XPS scan of carbon nitride was deconvolved into three peaks: 397.9 eV ($sp^2$ N); 399.7 eV ($sp^3$ N); and 403.8 eV (protonated $sp^2$ N). These $N_{1s}$ peak assignments were made using previous literature assignments of N-functionalities on $sp^2$ carbon. The unit cell for gh-$C_6N_9H_3$ (FIG. 1D) contains a total of 36 nitrogen atoms, of which 28 N atoms are $sp^2$ (pyridinic) and 8 N atoms are $sp^3$ (amino and graphitic). This composition (77.78% $sp^2$ N; 22.22% $sp^3$ N) is closely matched by the high-resolution $N_{1s}$ XPS peaks in which 78.19% of N atoms are pyrdinic (including protonated) and 21.81% are amino.

Without limitation to any mechanism, the protonated pyridine peak, which accounts for 2N atoms of the 36N atoms in the unit cell (FIG. 1D), may, for example, be explained by the extensive hydrogen bonding found throughout melon's polymer structure. It has been previously observed that H-bridging between pyridinic-N and carboxylic or phenol groups led to XPS peaks in the range 402-405 eV, similar to quaternary N peaks. There are 8 total H-bridges within the gh-$C_6N_9H_3$ unit cell between the N(—H)$_{(1-2)}$ groups and the pyridinic N groups of the heptazine subunits. Furthermore, proton transfer between the two H-bridges of the N—H groups and pyridinic N groups yields a tautomer stabilized by pi-bond resonance. The resulting average structure of the two tautomers (see FIG. 1D) may, for example, explain the protonated $sp^2$ N peak found at 403.8 eV because the two N—H groups of each tautomer are actually more like protonated $sp^2$ N groups due to pi-bond resonance.

In a number of representative embodiments, sensor devices were prepared by sequentially depositing rGO and exfoliated carbon nitride between interdigitated gold electrodes. rGO sheets used in this work were between 0.5-2 µm wide and contained structural defects such as wrinkles and grain boundaries on the graphitic basal plane (S4). The distance between interdigitated electrodes of the studied chemiresistor devices was 8 µm, thus requiring the deposition of several overlapping rGO sheets to bridge the electrodes. Effective deposition of rGO sheets between the interdigitated electrodes was tested by taking current-voltage (I-V) curves after the DEP procedure. A current in the µA range at 1 V was found to correspond to an ideal deposition, since lower currents represented an unreliably low concentration of rGO between the electrodes while higher currents represented too high rGO concentration resulting in sensor insensitivity. Carbon nitride was deposited on top of rGO sheets through a dropcast procedure.

Upon application of electromagnetic energy to the carbon nitride/rGO sensing medium systems hereof (in, for example, a humid $N_2$ environment in a number of studied embodiments), a significant increase in electrical conductance occurs. Without limitation to any mechanism, studies of a carbon nitride on a rGO in a photoelectrochemical set-up have showed that photoexcited electrons are generated in carbon nitride and transferred to the rGO sheet. In photocatalyst experiments, photogenerated holes remain on carbon nitride and oxidize water to oxygen gas, while the photogenerated electrons reduce oxygen to hydrogen peroxide on the rGO surface. The same charge separation from carbon nitride to rGO was observed in the studies of the carbon nitride/rGO sensing media hereof when studied as a chemiresistor. Charge transfer from carbon nitride to rGO was, for example, evidenced by large conductance increases of representative carbon nitride/rGO chemiresistors under UV irradiation. In dry nitrogen background, the conductance remains elevated even after the UV light is removed, indicating that charge recombination between photogenerated electrons and holes does not occur once the photogenerated electrons are separated onto the rGO surface. The work functions of carbon nitride and rGO were determined by taking valence XPS spectra of each material and comparing to copper foil's valence XPS spectrum. Determination of carbon nitride and rGO's approximate Fermi levels allows the comparison of each material's electronic bands against a standard electrode potential. Carbon nitride is a semiconductor with a ~2.7 eV bandgap while rGO is a semi-metal with little to no bandgap. Charge transfer from carbon nitride's conduction band to rGO places photoexcited electrons at a potential exceeding that of 4-e-reduction potential of $O_2$. In humid conditions, photogenerated holes on carbon nitride oxidize water to $O_2$. Water oxidation provides protons, thus allowing photoexcited electrons on rGO to reduce $O_2$ to $H_2O$ (or $H_2O_2$). The absence of protons in dry conditions prevents oxygen reduction, which corresponds to the lack of oxygen sensitivity in dry conditions (see, for example, FIG. 6B). Recovery toward baseline once UV irradiation is removed (see, for example, FIG. 6A) may, for example, also be understood with the photoredox mechanism. In humid conditions a small concentration of $O_2$ is present as a result of water oxidation while dry conditions are always anaerobic unless $O_2$ is introduced. According to the proposed photoredox mechanism (see FIG. 2), the sensor should have a response to $O_2$ concentrations as long as the rate of $O_2$ reduction exceeds the rate of charge transfer from carbon nitride to rGO.

Sensors hereof may, for example, be constructed as chemiresistors or field effect transistors. In a number of embodiments, chemically sensitive, solid-state resistors (chemiresistors) and field effect transistors (FETs) hereof exhibit room temperature gas sensitivity to determine oxygen levels. In FET devices or system, one, for example, measures electrical current under an applied gate voltage. In chemiresistor devices, a gate voltage is not applied. In the case of a chemiresistor device or system hereof, light energy (for example, light energy in the UV or visible spectrum may be applied to increase electrical conductance in the representative carbon nitride/rGO sensing medium systems hereof as described above. In the case of a FET device or system hereof, electrical energy may be applied (for example, via a gate voltage) to increase electrical conductance of the representative carbon nitride/rGO sensing medium systems hereof. In both types of devices, an electrical property (for example, conductance or resistance) of the sensing medium changes upon exposure to the chemical analyte, thereby providing a sensor signal.

A schematic representation of an FET sensor system 10 hereof is set forth in FIGS. 3A and 3B, while a chemiresistor sensor system 10*a* hereof is illustrated in FIG. 4. The illustrated sensor systems 10, 10*a* include a sensing medium material including a layer of an oxygen functionalized graphitic material such as rGO 20, 20*a* and a layer of graphitic carbon nitride 24, 24*a* between electrodes S and D, 40*a* and 40*a*′.

As illustrated in FIGS. 3A and 3B, the sensing medium or material hereof, may, for example, be disposed upon a substrate 30 (for example, silicon dioxide or quartz) and contacted by two conductive (for example, metallic—such as Au and/or Ti) electrodes representing a source (S) (a conductive electrode or terminal) and a drain (D) (a conductive electrode or terminal). In the operation of an FET circuit such as illustrated in FIGS. 1A and 1B, changes in electrical conductivity may, for example, be measured for an applied gate voltage. One may, for example, measure current flow between source (S) and drain (D) as a function of a swept/varied gate voltage range.

As described above, a chemiresistor device such as device 10*a* does not include an applied gate voltage. In chemiresistor 10*a* the sensing medium or material, including nanostructures 20a, bridges the gap between two conductive electrodes 40a and 40a' (for example, gold electrodes), which may be referred to a source and a drain. The sensing medium or material hereof may alternatively coat a set of interdigitated electrodes. The resistance/conductance between electrodes 40a and 40a' can be readily measured. A source 50a of light energy is provided to increase conduction in the sensing medium as described above. The resistance/conductance of the sensing medium is changed by the presence of the analyte.

As, for example, illustrated in FIG. 4, the sensor assembly may, for example, be placed in connection with a control/processing system 100 (for example, on a printed control board or PCB) via a connector or connector as known in the art. Control/processing system 100 includes a controller system or processor system 110 (including, for example, one or more microprocessors) and a memory system 120 which is placed in operative or communicative connection with processor system 110. Control/processing system 100 may also be in operative connection with a display 140 such as a liquid crystal display. A power supply/battery 130 may be supplied to power one or more electronic circuitry components as described above.

In a number of studies, a generally uniform distribution of carbon nitride nanosheets across the Si sensor chip was achieved with the dropcast procedure (see FIG. 5A), which provided similar sensing behavior among a number of studied chemiresistor devices. FIG. 5A provides an optical image of a representative carbon nitride/rGO sensor chip hereof. FIG. 5B provides a scanning electron microscopy (SEM) image of rGO decorated with carbon nitride nanoparticles or NPs between two Au electrodes. Exfoliation of the carbon nitride material was done with bath sonication of an aqueous dispersion. It was found that an hour of sonication was sufficient to exfoliate 1-3 μm carbon nitride sheets into 10-100 nm nanosheets. The carbon nitride nanosheets were found to deposit on the wrinkles and edges of the rGO sheet (FIGS. 5B and 5C). Wrinkles, grain boundaries, and edges of rGO are known to contain a higher concentration of defect sites and oxygen moieties as compared to flat basal plane regions of the rGO sheet. The carbon nitride nanosheets could be removed off the rGO with a water wash, making it unlikely that covalent bonds are formed between the two components. Adhesion between the carbon nitride nanosheets and rGO was more likely a result of H-bonding and/or electrostatic interactions between hydroxyl and carboxyl defect sites on rGO and the pyridinic N groups of carbon nitride.

Figure 6A:
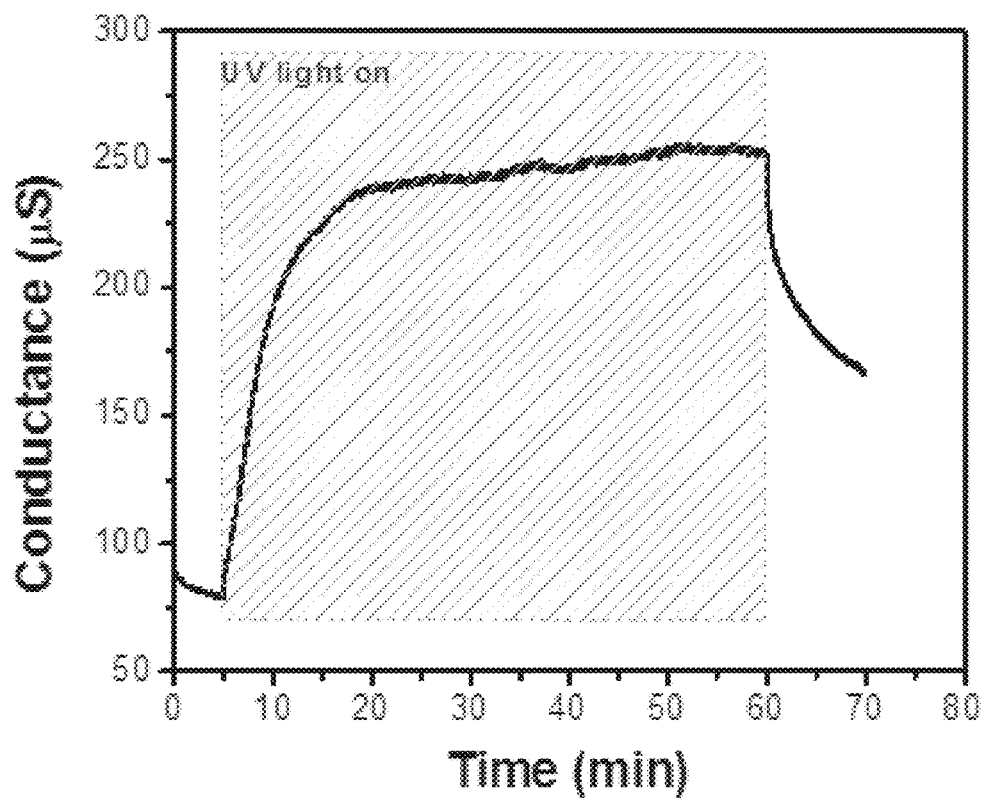
FIG. 6A illustrates conductance measurements as a function of time for oxygen sensing chemiresistor devices hereof including carbon nitride/rGO sensing media in humid $N_2$.

Carbon nitride/rGO chemiresistor devices were tested in various gas environments with and without UV irradiation. Though carbon nitride can be photoexcited with visible light, UV light (365 nm) was used in a number of studies because UV light has a cleaning effect on graphene by removing surface contaminants. When the carbon nitride/rGO chemiresistor was irradiated with UV light in a humid $N_2$ environment, a sharp increase in electrical conductance was observed (FIG. 6A). In the same experiment a saturation point in conductance is reached after 15 minutes of UV irradiation (6 W), which is more than double the initial conductance measured before UV irradiation. UV light is known to photoexcite carbon nitride; therefore, the increase in the chemiresistor's conductance can be explained by photogeneration of charge carriers in the carbon nitride nanosheets and subsequent transfer of charge carriers into the rGO transducer. In a humid nitrogen environment, the carbon nitride/rGO chemiresistor recovers back towards its baseline once UV light is removed. UV irradiation of a bare rGO chemiresistor showed a small decrease in conductance, likely a result of UV light's cleaning effect of surface contaminants. Therefore, the two-fold conductance increase of the carbon nitride/rGO chemiresistor under UV light is the result of charge carrier photogeneration in carbon nitride nanosheets. Likewise, the carbon nitride/rGO chemiresistor in dry nitrogen conditions also rose in conductance when irradiated with UV light; however, once the UV light was removed the chemiresistor shows little to no recovery back to baseline. The difference between baseline recovery post-UV light in humid nitrogen versus dry nitrogen indicates that $H_2O$, or a redox product of $H_2O$, is responsible for the baseline recovery.

Exfoliation of graphitic carbon nitride into nanosheets had an effect on the chemiresistor's photoexcitation behavior. Non-exfoliated graphitic carbon nitride/rGO chemiresistor in humid nitrogen showed a 32% increase in conductance when irradiated with UV light for five minutes. In comparison, exfoliated carbon nitride/rGO chemiresistor increased by 160% when irradiated with UV light for five minutes (FIG. 6A). This large difference in photoexcitation between non-exfoliated carbon nitride and exfoliated carbon nitride can be explained by several possible effects: 1) exfoliated carbon nitride absorbs more UV light than non-exfoliated carbon nitride due to a shift in bandgap; 2) exfoliation of carbon nitride into nanosheets "unstacks" carbon nitride such that there is a larger carbon nitride surface area; or 3) carbon nanosheets are able to form a better interface with rGO than non-exfoliated sheets because of their size (10-100 nm vs. 1-3 μm).

Figure 6B:
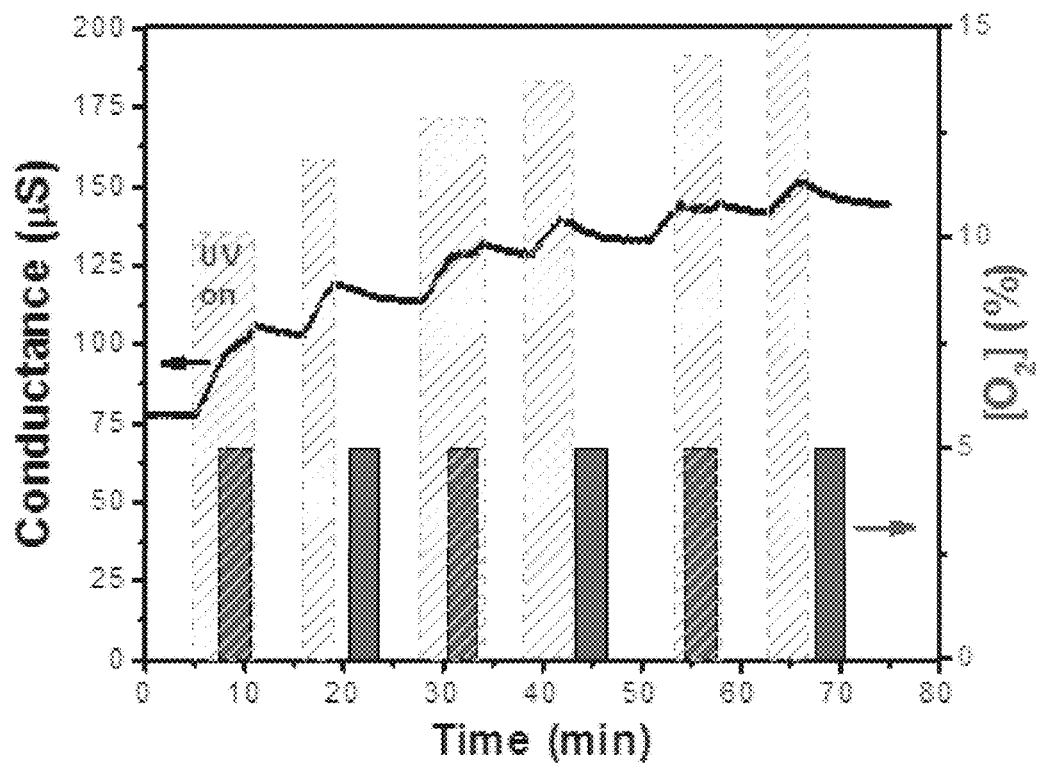
FIG. 6B illustrates conductance measurements as a function of time for oxygen sensing chemiresistor devices hereof including carbon nitride/rGO sensing media with 3 min exposures of $O_2$ in dry $N_2$.
Figure 6C:
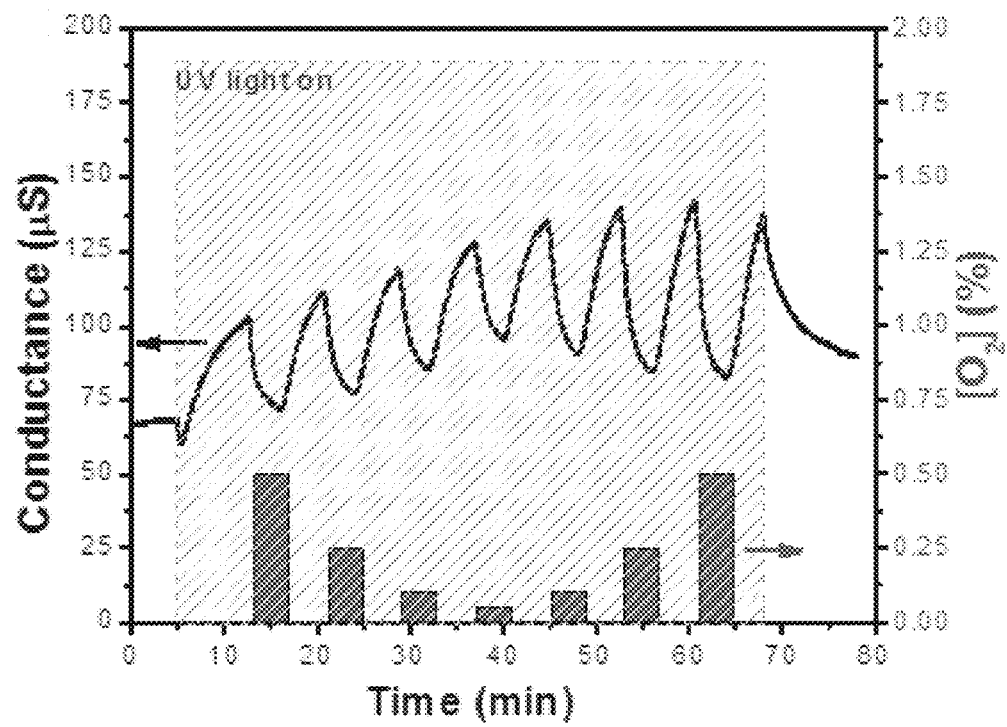
FIG. 6C illustrates conductance measurements as a function of time for oxygen sensing chemiresistor devices hereof including carbon nitride/rGO sensing media with 3 min exposures of $O_2$ in humid $N_2$.

As charge transfer from UV-irradiated carbon nitride into the rGO transducer was hypothesized, the carbon nitride/rGO chemiresistor was exposed to oxygen gas in both dry and humid conditions. Oxygen is an oxidizing gas that will react with photoexcited electrons if their potential is large enough. In dry $N_2$ background, 5% oxygen exposures with and without UV irradiation showed little to no effect on chemiresistor's conductance (FIG. 6B). In contrast, under humid conditions and UV light, the carbon nitride/rGO chemiresistor showed a large drop in conductance when exposed to oxygen (FIG. 6C). In the same experiment the conductance of the chemiresistor was found to increase once the oxygen exposure ended. A reversible response indicates that oxygen gas is not irreversibly adsorbed, but rather reacts with photoexcited electrons.

Figure 6D:
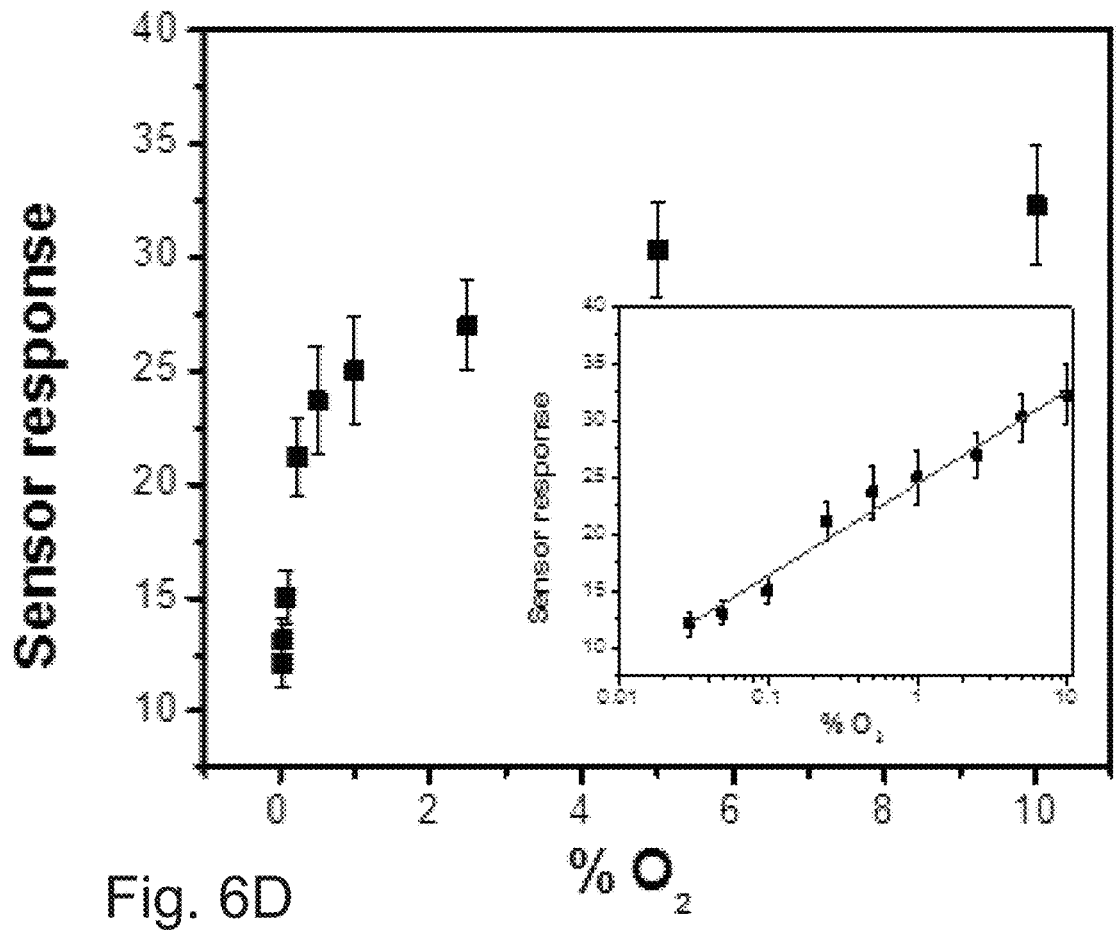
FIG. 6D illustrates sensor response (percent drop in G in first minute) vs. $O_2$ concentration, wherein, in the inset, the X-axis is changed to logarithmic scale to illustrate sensor response falling along logarithmic function.
Figure 7A:
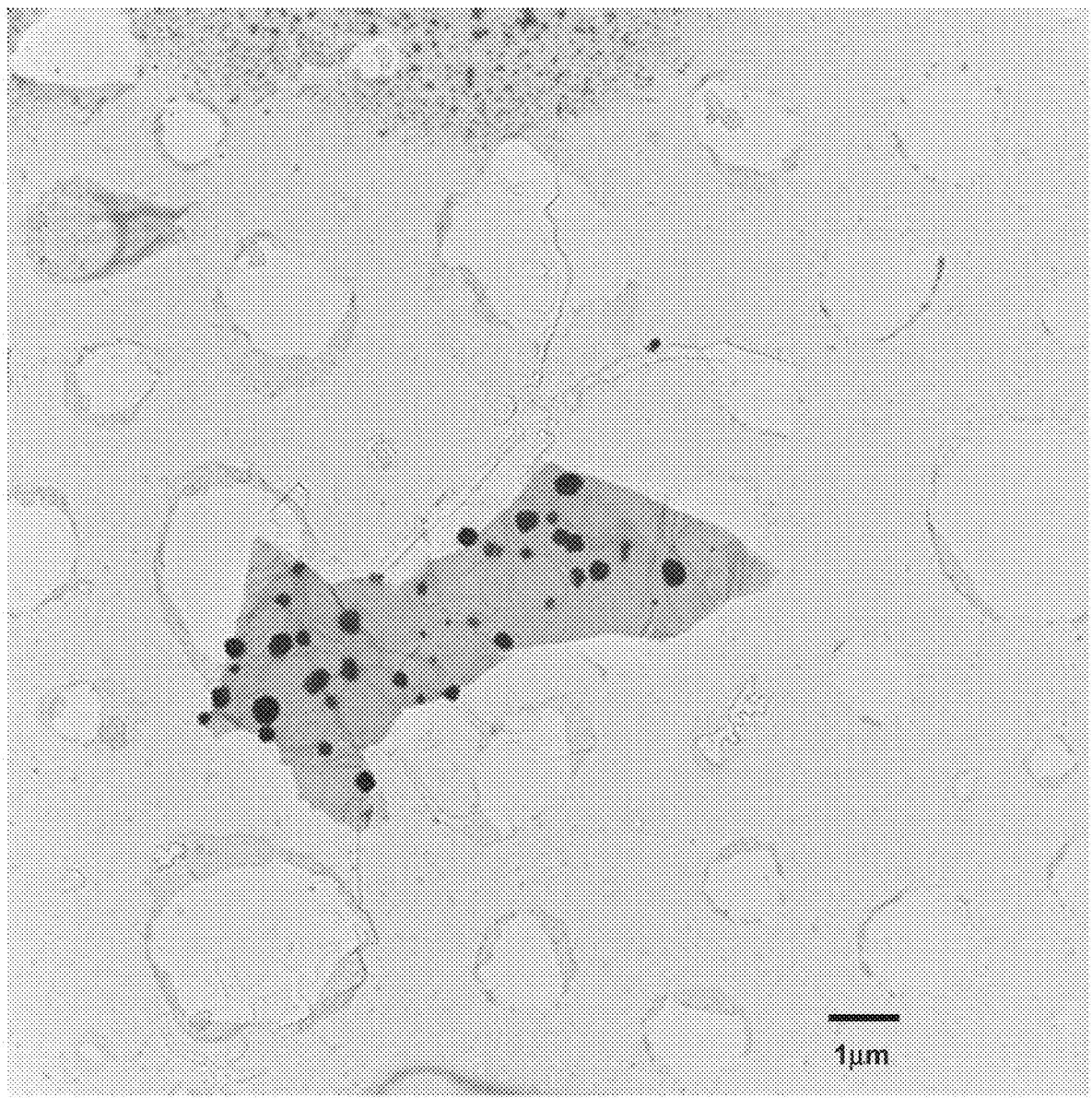
FIG. 7A illustrates a TEM image of rGO including deposited nanoparticles (NP) of copper (Cu).
Figure 7B:
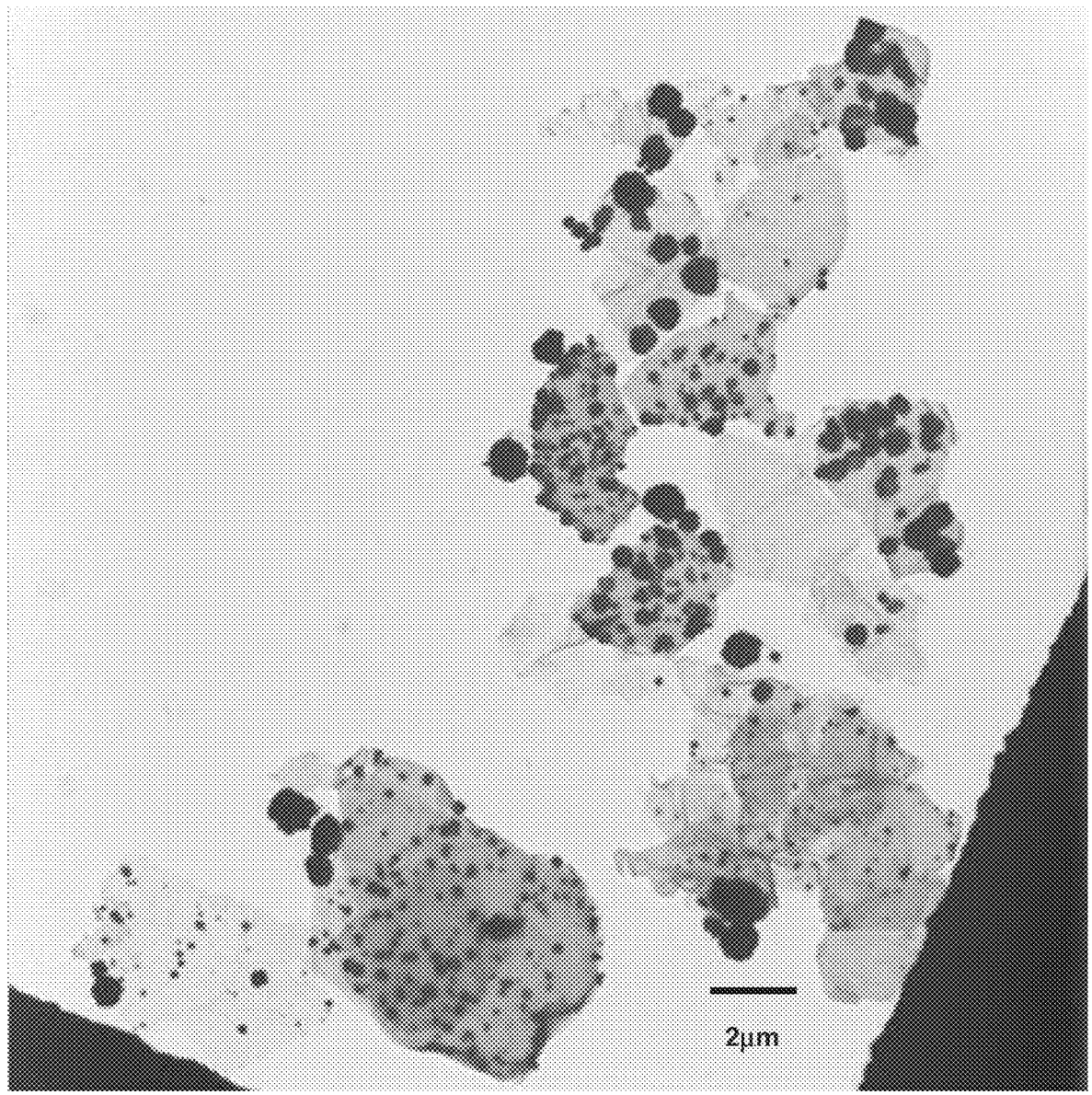
FIG. 7B illustrates another TEM image of rGO including deposited cu NP.
Figure 9A:
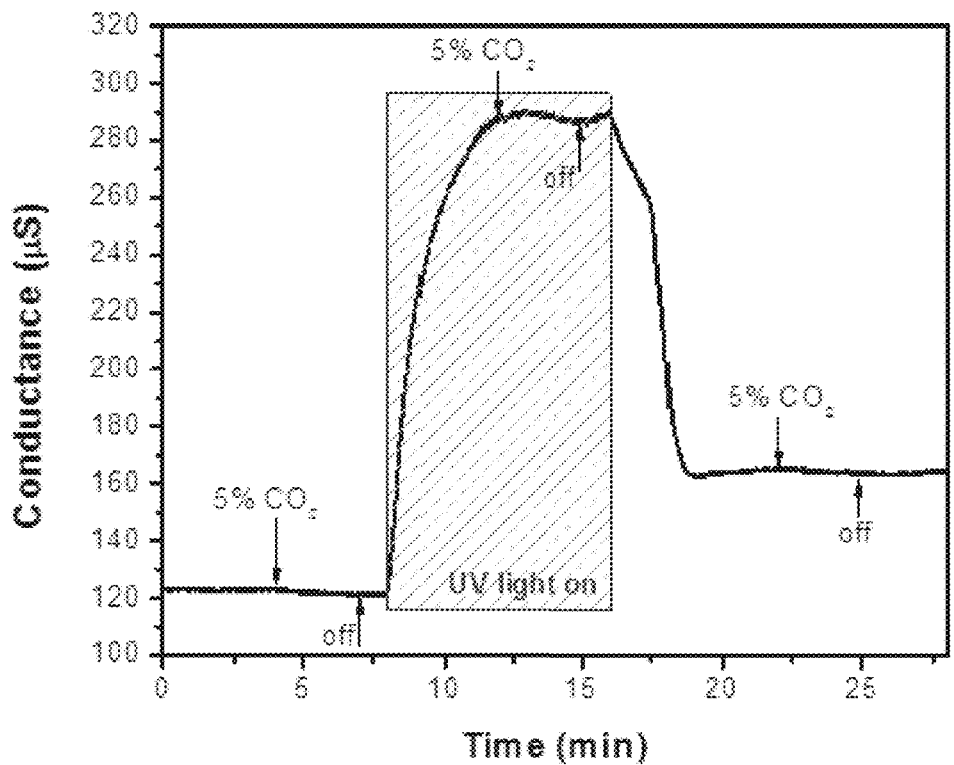
FIG. 9A illustrates $CO_2$ sensing in humid $N_2$ for sensing measurements of two carbon nitride/Cu NP/RGO devices.
Figure 9B:
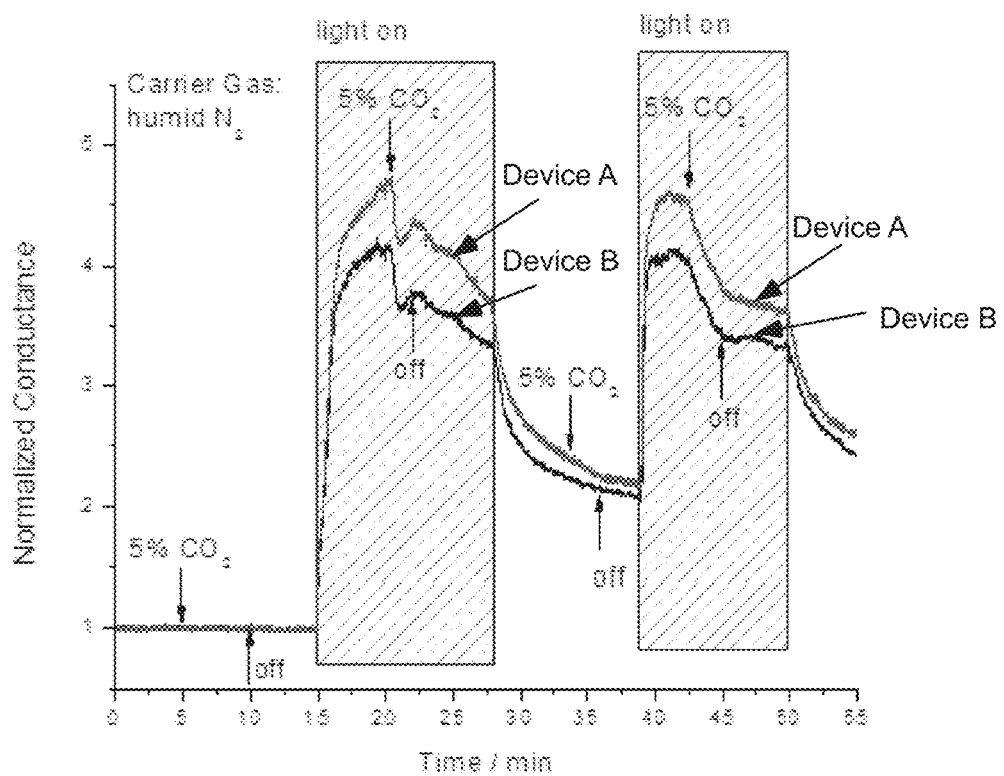
FIG. 9B illustrates $CO_2$ sensing measurements for one carbon nitride/RGO device.

A set of 3-minute exposures of oxygen concentrations ranging from 300-100,000 parts per million (ppm) were tested. The response (eq. 1) of the chemiresistor in the first minute of oxygen exposure was found to be logarithmically proportional to oxygen concentration (FIG. 6D).

$$\text{sensor response} = \frac{G_{0\,min\,after\,exposure} - G_{1\,min\,after\,exposure}}{G_{0\,min\,after\,exposure}} \quad \text{(eq. 1)}$$

Each chip had four chemiresistor devices which allowed four simultaneous sensor responses to every oxygen exposure. The limit of quantification (LOQ) for this sensor, assuming the logarithmic function (eq. 2) continues for concentrations >300 ppm, was found to be 20 ppm. LOQ was determined as the oxygen concentration that exceeds ten times $SD_{blank}$ ($10SD_{blank}=0.015$).

$$\text{sensor response} = 3.575 \ln(O_2 \text{ vol \%}) + 24.59 \quad \text{(eq. 2)}$$

The carbon nitride/functionalized graphitic materials hereof may be modified to, for example, modify the work function of the resulting composite material to, for example, sense other targets or analytes. The carbon nitride/functionalized graphitic materials hereof may, for example, be modified by depositing metal particles/nanoparticles upon the functionalized graphitic material. Deposited metal nanoparticles that may modify the work function include copper (Cu), gold (Au), palladium (Pd), and platinum (Pt). In addition to metallic NPs, inorganic semiconducting nanoparticles such as gallium phosphide (GaP), cadmium sulfide (CdS), copper (I) oxide ($Cu_2O$), or copper iron oxide ($CuFeO_2$) may be attached to form a Z-scheme for $CO_2$ photoredox sensing. In that regard, representative modification of the carbon nitride/reduced graphene oxide (RGO) material was demonstrated by in situ growth of copper nanoparticles (Cu NPs) on the RGO layer prior to depositing the carbon nitride layer. Cu NP/RGO was synthesized as follows: first, graphene oxide (GO) was incubated with copper (II) chloride hydrate at a pH of 10; second, hydrazine hydrate was added to simultaneously reduce graphene oxide and copper (II) to Cu NP/RGO. FIG. 1 shows a TEM image of the resultant material: Cu NP/rGO.

Figure 2:
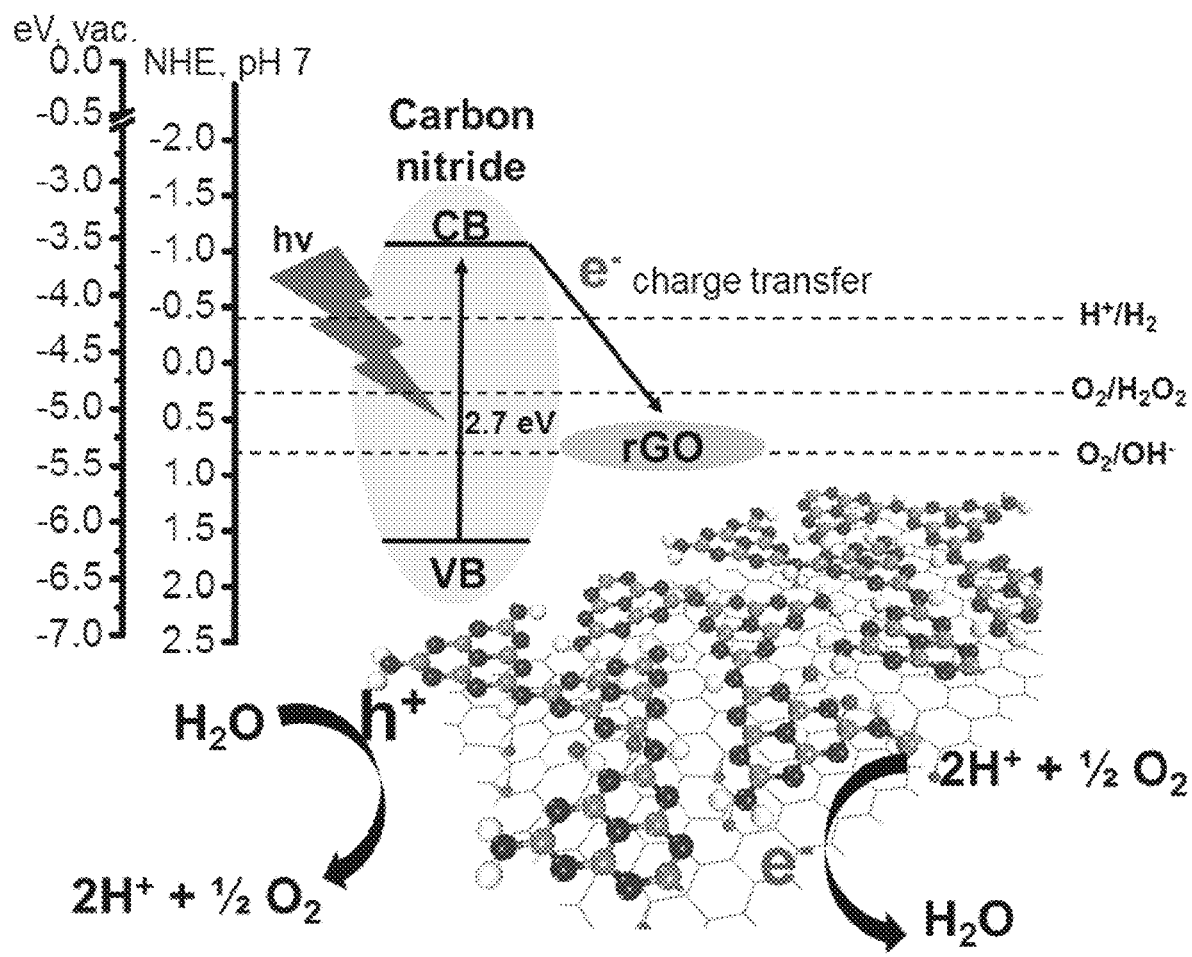
FIG. 2 illustrates, without limitation, an embodiment of a proposed photoredox mechanism for oxygen sensing on photoexcited carbon nitride/rGO.

This composite material was analyzed by X-ray photoelectron spectroscopy (XPS) in order to determine whether appending the Cu NPs modulated the work function of the resulting composite. Analysis of the valence XPS spectrum indicated that Cu NP/RGO has a work function of 5.18 eV, which is between that of bare RGO (5.31 eV) and pure Cu (4.65 eV). This supports the conclusion that RGO's work function can be shifted by appending metallic NPs. FIG. 2 shows the valence XPS spectrum of Cu NP/RGO and a table of Cu, RGO, and Cu NP/RGO work functions.

Cu NP/RGO was deposited on interdigitated gold electrode silicon chips through dielectrophoresis, and carbon nitride was subsequently dropcast on top. This device preparation procedure is the same as previously described with the only exception being the deposition of Cu NP/RGO instead of bare RGO. The resulting chemiresistor device (carbon nitride/Cu NPs/RGO) was tested in the laboratory gas sensor set-up for carbon dioxide sensitivity. When irradiated with UV light, the chemiresistor device conductance increased by more than four times the baseline conductance. When the device was exposed to 3 minute bursts of 5% $CO_2$ in humid $N_2$, the conductance dropped 16%. Without UV irradiation, the chemiresistor was insensitive to 5% $CO_2$. A control was done with carbon nitride/RGO (no Cu NPs), and the chemiresistor device was insensitive to 5% $CO_2$, even with UV irradiation. FIG. 3 shows the sensor results of two carbon nitride/Cu NP/RGO devices and the sensor result for one carbon nitride/RGO device.

Furthermore, oxygen sensors hereof demonstrate selectivity for the detection of oxygen in the presence of potential interferants such as $CO_2$ and $H_2$. Large concentrations of $CO_2$ and $H_2$ (5 vol. %) exposed to the carbon nitride/rGO chemiresistor showed little to no change in conductance. Oxidizing gas species that have higher reduction potentials than rGO's conduction band minimum, such as $CO_2$, will not affect the conductance of the rGO transducer. Reducing gases, such as $H_2$, will not affect the rGO transducer. However, at high enough concentrations, reducing gases may interact with the valence band of the carbon nitride layer.

EXPERIMENTAL

Synthesis and Preparation of Exfoliated "Graphitic" Carbon Nitride.

Dicyandiamide (DCDA, 99% purity, 1 gram; Sigma-Aldrich) was placed in an open quartz boat, which was subsequently placed in a quartz tube. The quartz tube atmosphere was replaced with argon and the tube was sealed on both ends by water bubblers. The sample was heated in a CVD furnace (Lindberg blue 3-zone furnace) for 2 hours at 550° C. and left to cool overnight. The remaining pale-yellow solid (~140 mg) was recovered from the quartz boat and ground in a mortar and pestle for ~10 minutes to yield a fine powder. In order to exfoliate the bulk sheets into nanosheets, the resultant carbon nitride powder was dispersed in nanopure water (100 µg/mL) and sonicated in a bath sonicator for 1 hour.

Preparation of rGO/Carbon Nitride Chemiresistor Devices.

rGO was prepared through a previously described chemical reduction method. Briefly, graphene oxide (5 mL, 3 mg/mL in $H_2O$; Graphene Supermarket) is stirred with 5 µL of hydrazine hydrate (ca. 51° %/hydrazine; Acros Organics) in an 80° C. oil bath for 3 hours. The black precipitate (rGO) is collected through vacuum filtration and dispersed in DMF. Si chips, each containing 4 devices with interdigitated Au electrodes, were fabricated in-house and connected to 40 CERDIP packages with Au wires. 3 µL of rGO (0.1 mg/mL in DMF) is dropped above the chip and, via dielectrophoresis (DEP; 10 $V_{pp}$, 300 kHZ, 10 seconds), rGO sheets are deposited between the interdigitated electrodes. Exfoliated carbon nitride is deposited above rGO on the devices by dropcasting 3 µL of exfoliated carbon nitride (0.1 mg/mL in $H_2O$) on top of the chip and evaporating off the solvent by placing the packaged chip on a 130° C. hotplate.

Characterization. Electron Microscopy.

Transmission electron microscopy (TEM) samples were prepared by dropcasting 7 µL of diluted samples in water on TEM sample grids (carbon film, 400 mesh copper grid; Electron Microscopy Sciences). The TEM instrument model used was FEI Morgagni. Scanning electron microscopy (SEM) of rGO/carbon nitride was performed directly on the Si chip. The SEM instrument model used was JEOL JSM6510.

Powder x-Ray Diffraction (PXRD).

PXRD was performed on a Bruker D8 XRD system equipped with LynxEye detector. Powder carbon nitride on a glass slide was the sample tested. 2θ angles between 8° and 60° were measured at 0.020 intervals with a rate of 0.3 seconds/point. The x-ray source was Cu Kα held at 40 kV and 40 µA with a 0.2 mm aperture slit width.

Fluorescence Spectroscopy.

Photoluminescence measurements were obtained using a Nanolog spectrofluorometer (HORIBA Jobin Yvon) equipped with a xenon lamp (400 W) light source, double excitation monochromators, and R928 Hamamatsu visible light detector. In order to test solid samples, a custom-made integrating sphere with quartz tube solid sample holders was used as an accessor to the spectrofluorometer. Spectra were obtained by exciting the sample with a single wavelength (300, 320, 340, 360, or 380 nm) while the emission wavelength was scanned from 400 to 600 nm at 2 nm increments.

X-Ray Photoelectron Spectroscopy (XPS).

XPS was performed on an ESCALAB 250Xi. Carbon nitride powder samples were placed directly onto copper tape, which were subsequently fixed onto the XPS sample holder. rGO samples were dropcast from DMF solution onto copper foil and subsequently secured onto the XPS sample holder with copper tape. An electron flood gun was run simultaneously with the experiment to allow charge compensation. Survey, valence, high-res $C_{1s}$ and $N_{1s}$ were collected for carbon nitride samples. Survey and valence scans were collected for rGO. Valence scan was collected for Cu foil. Due to surface contamination on the surface of Cu and rGO, an Ar ion etching treatment (3000 eV, 60 seconds) was applied before collecting the XPS data.

Solid-State Nuclear Magnetic Resonance.

Solid-state NMR was done on a Bruker AVANCE 500 wide-bore instrument with a 4 millimeter CP-MAS probe. $^{1}H-^{13}C$ and $^{1}H-^{15}N$ experiments were done at 8 kHz spin. $^{1}H-^{13}C$ peaks were referenced to the standard glycine peak of 176.5 ppm. $^{1}H-^{15}N$ peaks were referenced to the standard glycine peak of 32.3 ppm.

Oxygen Sensing Experiment Set-Up.

Packaged rGO/carbon nitride chemiresistor chips were placed on a test board and sealed in a Teflon chamber. The test board was connected to a Keithley Dual SourceMeter 2602 and Keithley Switching Matrix 708A, which were controlled with Labview software. This set-up extracts 4 data outputs simultaneously, allowing changes in electrical conductance of each chemiresistor device to be collected with Zephyr data-acquisition software (http://zephyr.sourceforge.net). Two gas flow controllers were used to control the concentration of oxygen in the Teflon test chamber. The diluting gas flow controller was connected to dry $N_2$ and the experimental gas flow controller was connected to dry air (for concentrations 1-5% $O_2$) or 1% $O_2$ in dry $N_2$ (for concentrations 0.05-0.5% $O_2$). In order to humidify the gas, a water bubbler filled with DI $H_2O$ was connected in-line before the Teflon chamber. The gas velocity was kept at 540 standard cubic centimeters per minute (sccm) for all experiments. The bias voltage for all experiments was 50 mV.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A sensor, comprising:
a substrate,
a first electrode,
a second electrode spaced from the first electrode,
a sensing medium on the substrate between the first electrode and the second electrode, the sensing medium comprising a functionalized graphitic material and an uncondensed graphitic carbon nitride disposed upon the functionalized graphitic material,
a system for applying electromagnetic energy to the sensing medium to increase the conductance of the sensing medium, and
circuitry comprising at least one measurement system in operative connection with the sensor to measure a variable relatable to the conductance of the sensing medium which is dependent upon the presence of an analyte to be detected.

2. The sensor of claim 1 wherein the functionalized graphitic material comprises oxygen functional groups.

3. The sensor of claim 1 wherein the functionalized graphitic material is reduced graphene oxide or holey reduced graphene oxide.

4. The sensor of claim 1 wherein the functionalized graphitic material is holey reduced graphene oxide.

5. The sensor of claim 1 wherein the functionalized graphitic material is holey reduced graphene oxide and the hole size of the holey reduced graphene oxide is within a predetermined range to provide a band gap within a predetermined range to determine an identity of the analyte.

6. The sensor of claim 1 wherein the analyte is oxygen.

7. The sensor of claim 6 wherein the system for applying electromagnetic energy is configured to apply UV light energy, visible light energy or electrical energy.

8. The sensor of claim 1 further comprising a humidity sensor.

9. The sensor of claim 1 further comprising a material deposited upon the functionalized graphitic material to alter the work function of the sensing medium.

10. The sensor of claim 9 wherein the material deposited upon the functionalized graphitic material comprises metal nanoparticles or an inorganic semiconductor nanoparticles.

11. The sensor of claim 10 wherein the metal nanoparticles comprise copper and the analyte is carbon dioxide.

12. A method of sensing an analyte, comprising:
providing a sensor system comprising a substrate, a first electrode, a second electrode spaced from the first electrode, and a sensing medium on the substrate between the first electrode and the second electrode, the sensing medium comprising a functionalized graphitic material and an uncondensed graphitic carbon nitride disposed upon the functionalized graphitic material,
applying electromagnetic energy to the sensing medium to increase the conductance of the sensing medium, and
measuring a variable relatable to the conductance of the sensing medium which is dependent upon the presence of the analyte to be detected.

13. The method of claim 12 wherein the functionalized graphitic material comprises oxygen functional groups.

14. The method of claim 12 wherein the functionalized graphitic material is reduced graphene oxide or holey reduced graphene oxide.

15. The method of claim 12 wherein the functionalized graphitic material is holey reduced graphene oxide.

16. The method of claim 12 wherein the functionalized graphitic material is holey reduced graphene oxide and the hole size of the holey reduced graphene oxide is within a predetermined range to provide a band gap within a predetermined range to determine an identity of the analyte.

17. The method of claim 12 wherein the analyte is oxygen.

18. The method of claim 12 wherein applying electromagnetic energy comprises applying UV light energy, visible light energy or electrical energy.

19. The method of claim 12 further comprising measuring humidity in the environment surrounding the sensing medium.

20. The method of claim 12 further comprising providing water to increase the humidity in the environment surrounding the sensing medium.

21. The method of claim 19 further comprising providing water to increase the humidity in the environment surrounding the sensing medium.

22. The method of claim 12 wherein a material is deposited upon the functionalized graphitic material to alter the work function of the sensing medium.

23. The method of claim 22 wherein the material deposited upon the functionalized graphitic material comprises metal nanoparticles or inorganic semiconductor nanoparticles.

24. The method of claim 23 wherein the metal nanoparticles comprise copper and the analyte is carbon dioxide.

* * * * *